(12) United States Patent
Flower et al.

(10) Patent No.: US 7,732,485 B2
(45) Date of Patent: Jun. 8, 2010

(54) TREATMENT OF CANCER

(75) Inventors: Kevin Flower, Derbyshire (GB); Alan McGown, Manchester (GB)

(73) Assignee: The University of Manchester, Manchester (GB)

( * ) Notice: Subject to any disclaimer, the term of this patent is extended or adjusted under 35 U.S.C. 154(b) by 169 days.

(21) Appl. No.: 10/583,686

(22) PCT Filed: Dec. 20, 2004

(86) PCT No.: PCT/GB2004/005440

§ 371 (c)(1),
(2), (4) Date: Jun. 19, 2006

(87) PCT Pub. No.: WO2005/058421

PCT Pub. Date: Jun. 30, 2005

(65) Prior Publication Data

US 2007/0142336 A1 Jun. 21, 2007

(30) Foreign Application Priority Data

Dec. 19, 2003 (GB) ................................ 0329416.2

(51) Int. Cl.
*A01N 55/02* (2006.01)
(52) U.S. Cl. ..................................................... 514/495
(58) Field of Classification Search ........................ None
See application file for complete search history.

(56) References Cited

U.S. PATENT DOCUMENTS

| 4,902,675 A | 2/1990 | Hill et al. |
| 2003/0114695 A1 | 6/2003 | Leung et al. |
| 2004/0063681 A1 | 4/2004 | Che |

FOREIGN PATENT DOCUMENTS

| EP | 0189306 A2 | 7/1986 |
| WO | 0078306 A1 | 12/2000 |

OTHER PUBLICATIONS

Vicente et. al. , Journal of Organometallic Chemistry (2002) 663:40-45.*
Dorwald F. A., Side reactions in organic synthesis, 2005, Wiley, VCH, Weinheim, p. IX of Preface.*
Barnard, Peter J., et al. "Mitochondrial permeability transition induced by dinuclear gold(I)-carbene complexes: potential new antimitochondrial antitumour agents." Journal of Inorganic Biochemistry 98(10), pp. 1642-1647, 2004.
Schmidbaur, H., et al. "Some Gold I Complexes of Phosphorus Ylides and their Effect in Gold Therapy with the Adjuvant Arthritis Model." Zeitschrift Fuer Naturforschung Teil B Anorganische Chemie Organische Chemie, vol. 33, No. 11, 1978, pp. 1325-1329.
Rozenberg, V. I., et al. "Mono(tin)- and bis(gold)-metalated covalently bonded .sigma.-aryl derivatives in the '2.2! paracyclophane series." Metallooranischeskaya Khimiya, 4(3), pp. 686-688, 1991 with English abstract.
Cagnoli, Monica, et al. "Synthesis and biological activity of gold and tin compounds in ovarian cancer cells" Anti-Cancer Drugs, 9(7), pp. 603-610, 1998.
International Search Report for PCT/GB2004/005440, dated Jun. 10, 2005.
Hrubisko, M., et al. "The role of metallothionein, glutathione, glutathione S-Transferases and DNA repair in resistance to platinum drugs in a series of L1210 cell lines made resistant to anticancer platinum agents." Biochemical Pharmacology, vol. 45, pp. 253-256, 1993.
Fink, D., et al. "The role of DNA mismatch repair in drug resistance." Clinical Cancer Research, vol. 4, pp. 1-6, 1998.
Shaw, C. Frank III, "Gold-Based Therapeutic Agents." Chemical Reviews, pp. 2589-2600, 1999.
Tiekink, Edward R.T. "Gold Derivatives For The Treatment Of Cancer," Critical Reviews in Oncology/Hematology, pp. 225-248, 2002.
Marcon, Giordona, et al. "Gold (III) Complexes As A New Family Of Cytotoxic And Antitumor Agents," Expert Reviews in Anticancer Therapy, pp. 337-346, 2002.
Colella G., et al. "Mismatch repair deficiency is associated with resistance to DNA minor groove alkylating agents." British Journal of Cancer, pp. 338-343, 1999.
Alley, Michael C., et al. "Feasibility Of Drug Screening With Panels Of Human Tumor Cell Lines Using A Microculture Tetrazolium Assay." Cancer Research, pp. 589-601, 1988.
Ostling, O., et al. "Microelectrophoretic Study Of Radiation-Induced DNA Damages In Individual Mammalian Cells." Biochemical and Biophysical Research Communications, vol. 123, pp. 291-298, 1984.
McKelvey-Martin, V. J., et al. "The Single Cell Gel Electrophoresis Assay (Comet Assay): A European Review." Mutation Research, pp. 47-63, 1993.
Collins, Andrew R., et al. "In Vitro Repair Of Oxidative And Ultraviolet-Induced DNA Damage In Supercoiled Nucleoid DNA By Human Cell Extract." Biochimica Et Biophysica Acta, pp. 724-727, 1994.
Olive, Peggy L., et al. "Sizing Highly Fragmented DNA In Individual Apoptotic Cells Using The Comet Assay And A DNA Crosslinking Agent." Experimental Cell Research, pp. 19-26, 1995.
Ward, Timothy H., et al. "Comet Assay Studies on the Activation of Two Diaziridinylbenzoquinones in K562 Cells." Biochemical Pharmacology, pp. 1115-1121, 1997.
Olive, Peggy L., et al. "Heterogeneity In Radiation-Induced DNA Damage And Repair In Tumor And Normal Cells Measured Using The 'Comet' Assay." Radiation Research, pp. 86-94, 1990.
Uson, Rafael, et al. "(Tetrahydrothiophene)Gold(I) Or Gold(III) Complexes." Inorganic Synthesis, pp. 85-91, 1989.
Bardaji, Manuel., et al. "Synthesis Of 2,4,6-tris(Trifluoromethyl)Phenyl Complexes Of Gold And Thallium." Journal of Organometallic Chemistry, pp. 1-7, 2002.

* cited by examiner

*Primary Examiner*—Frederick Krass
*Assistant Examiner*—Marcos Sznaidman
(74) *Attorney, Agent, or Firm*—Michael Best & Friedrich LLP

(57) ABSTRACT

The invention relates to the treatment of cancers, in particular, cancers that are resistant to platinum based chemotherapeutic agents. A pharmaceutical composition for the treatment of cancer comprising an effective amount of a compound having two gold(I) atoms each covalently bonded to a carbon atom in a covalent link connecting the two gold(I) atoms and a pharmaceutically acceptable excipient.

2 Claims, 9 Drawing Sheets

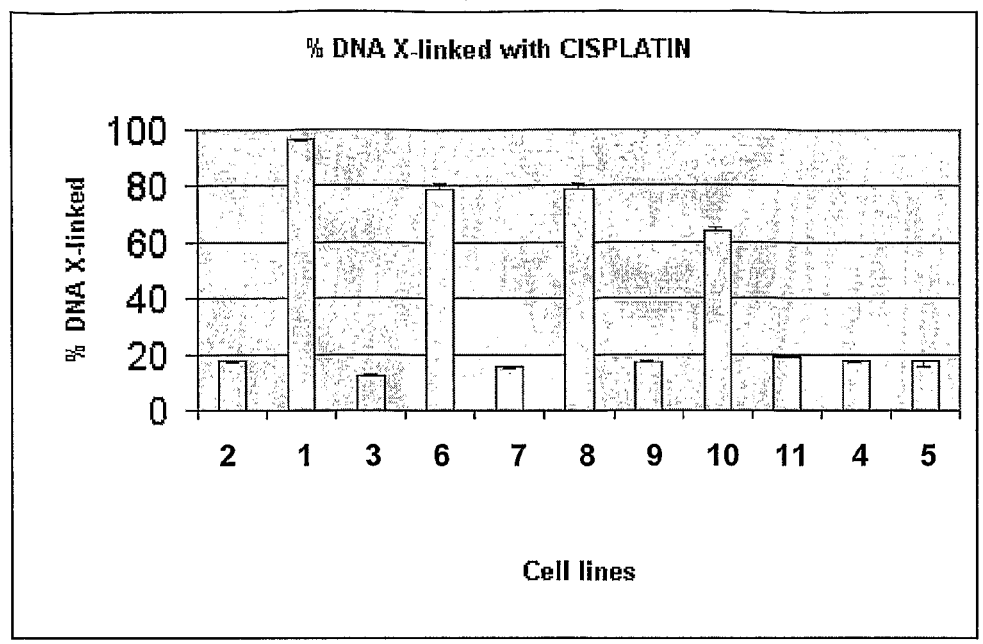
Figure 1. DNA cross-linking in parental and resistant cell lines following treatment with cisplatinum.

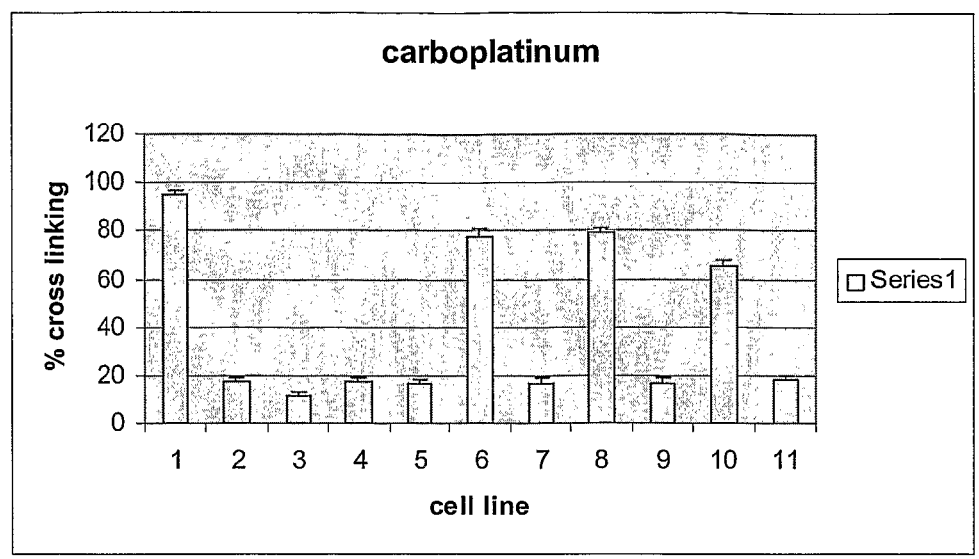
Figure 2. DNA cross-linking in parental and resistant cell lines following treatment with carboplatin.

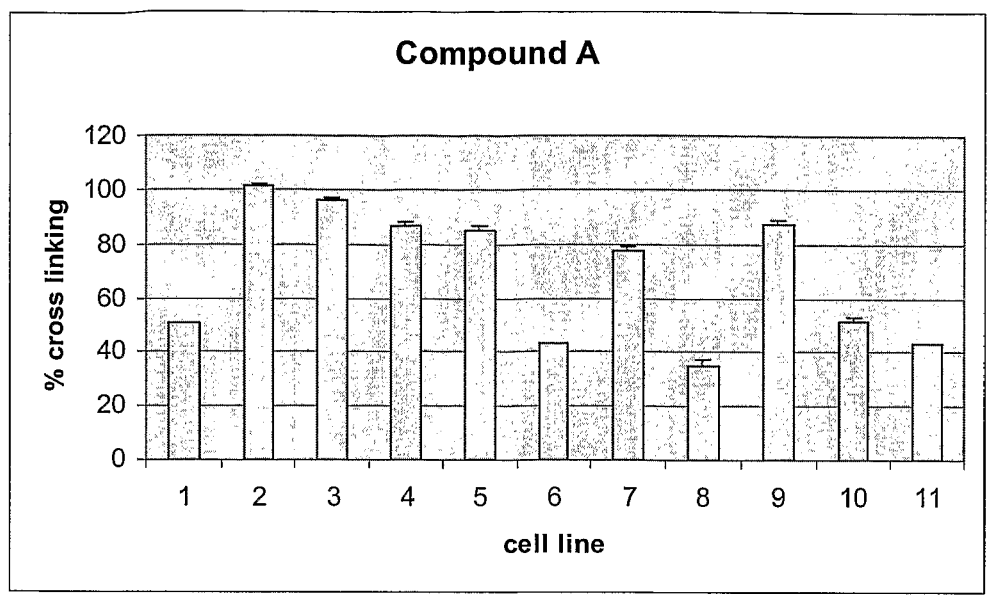
Figure 3. DNA cross-linking in parental and resistant cell lines following treatment with compound A.

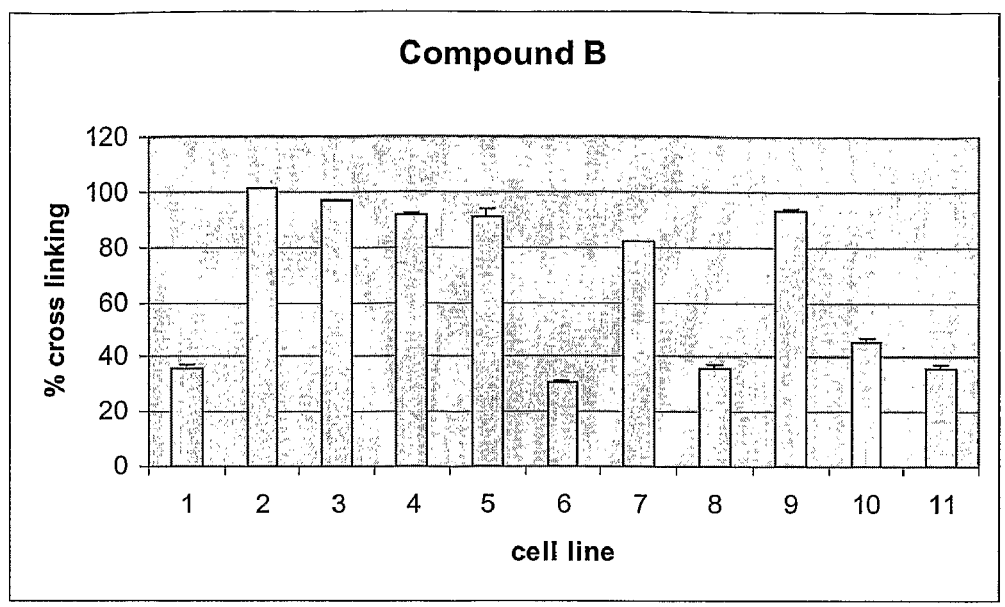
Figure 4. DNA cross-linking in parental and resistant cell lines following treatment with compound B.

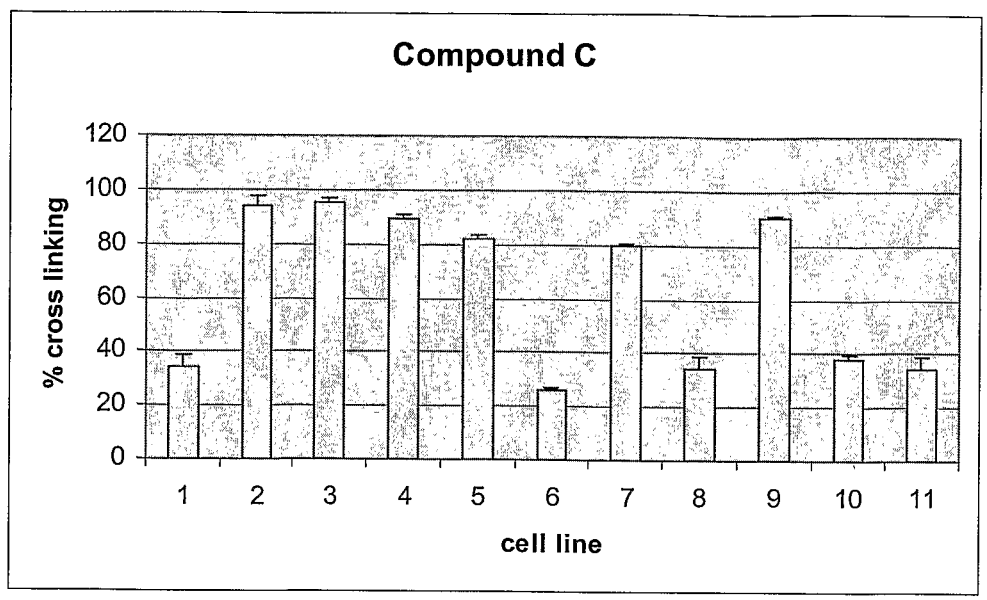
Figure 5. DNA cross-linking in parental and resistant cell lines following treatment with compound C.

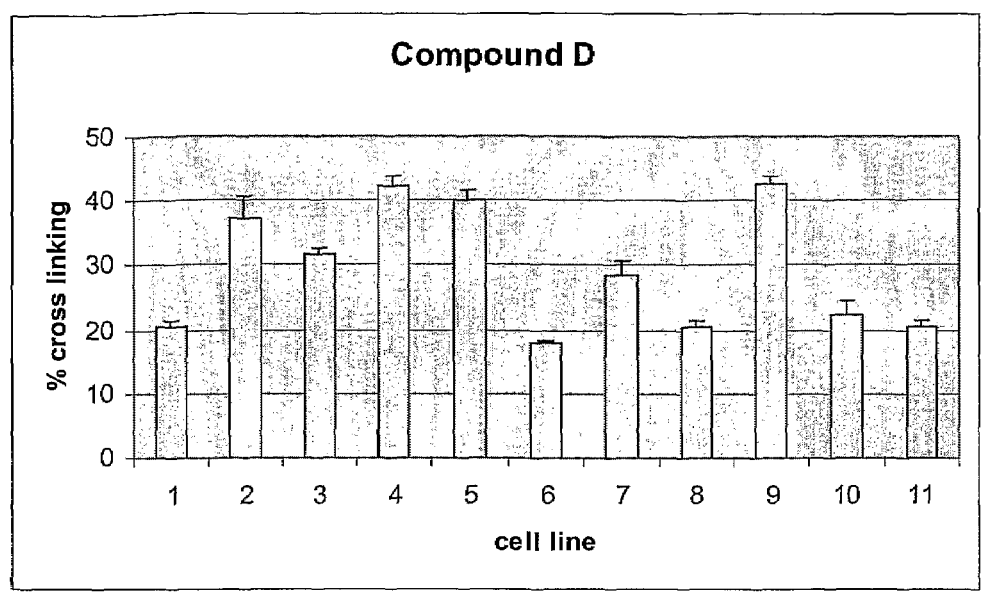
Figure 6. DNA cross-linking in parental and resistant cell lines following treatment with compound D.

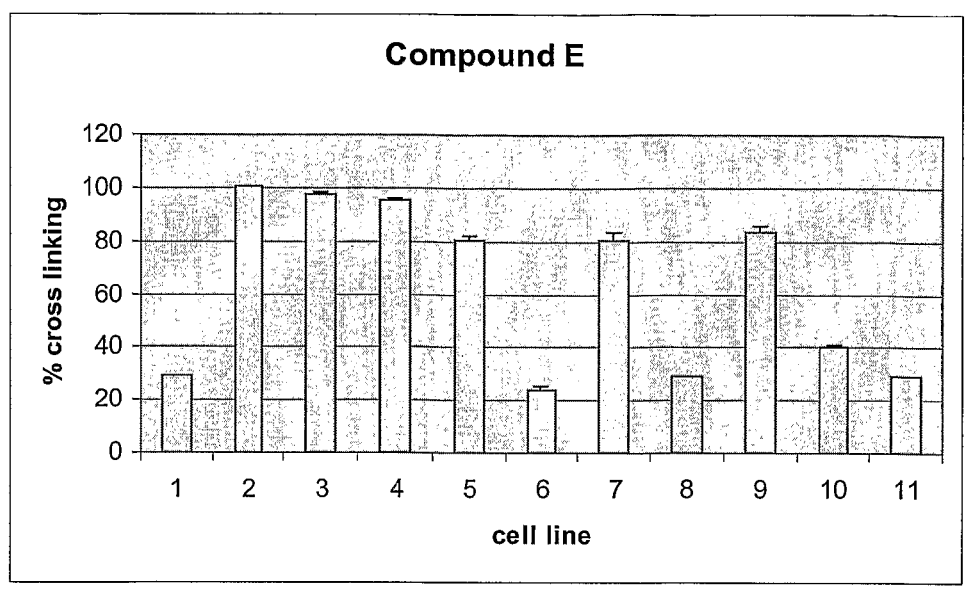
Figure 7. DNA cross-linking in parental and resistant cell lines following treatment with compound E.

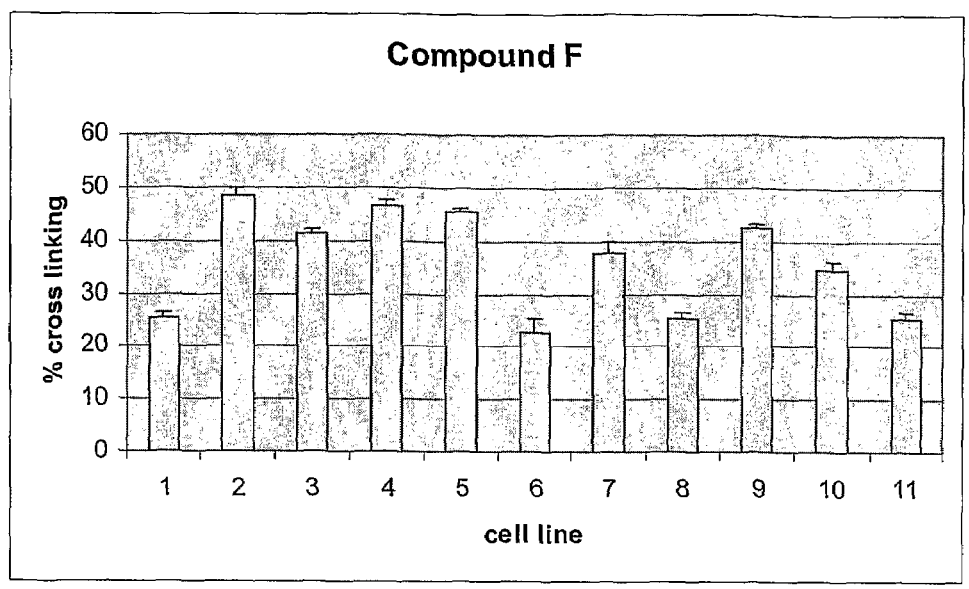
Figure 8. DNA cross-linking in parental and resistant cell lines following treatment with compound F.

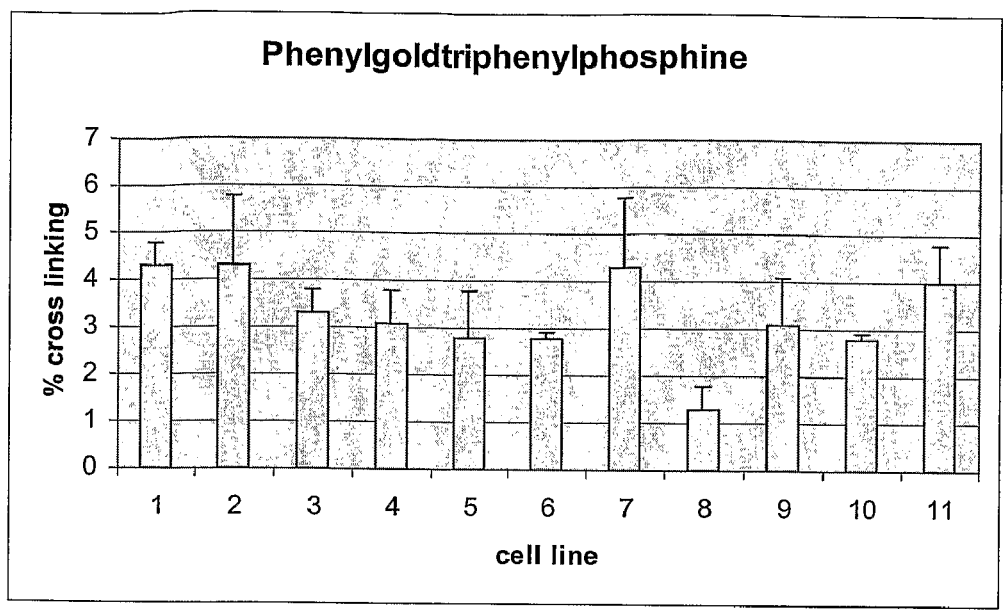
Figure 9. Comparative Example. DNA cross-linking in parental and resistant cell lines following treatment with compound Phenylgoldtriphenylphosphine (PAuP).

TREATMENT OF CANCER

CROSS-REFERENCE TO RELATED APPLICATIONS

This patent application is a national stage filing under 35 U.S.C. 371 of International Application No. PCT/GB2004/005440, filed Dec. 20, 2004, which claims foreign priority to United Kingdom Application No. 0329416.2, filed Dec. 19, 2003, the disclosures of which are incorporated by reference herein in their entireties. Priority to each application is hereby claimed.

The present invention relates to the treatment of cancer, more particularly but not exclusively, treatment of cancers that are resistant to platinum based chemotherapeutic agents.

The platinum drugs (e.g. cisplatinum and carboplatinum, also known as cisplatin and carboplatin respectively) are widely used and clinically active anti-tumour agents. Their activity is based on the ability to cross-link DNA so as to inhibit DNA replication or transcription thus hindering cell proliferation and slowing tumour growth.

One limitation to the activity of the platinum drugs is the development of resistance, resulting in a decrease or loss of anti-tumour activity. The biochemical and pharmacological changes that give rise to resistance to the platinum agents are complex and a number have been described including increased glutathione, altered DNA repair processes, and metallothioneins.[1] One DNA repair process that has been implicated is the loss or reduction of DNA mismatch repair.[2] The development of new therapies that can overcome or circumvent this resistance would have an implication on the treatment in a number of human cancers, including ovarian and lung cancer.

The use of gold-based compounds in cancer chemotherapy has been based upon a series of rationales: analogies between square planar-based Pt(II) and Au(III); analogy to the imunomodulatory effects of Au(I); and complexation of both Au(I) and Au(III) to known anti-tumour agents.[3] The use of Au(I)-based compounds in cancer treatment has focused upon compounds that contain phosphorus, sulfur-based ligand sets that are achiral or chiral, or upon biologically relevant ligands.[4] To-date the use of organometallic gold-containing complexes has centered on the use of Au(III) systems due to their structural and electronic similarities to the known Pt(II)-based systems such as cisplatin and carboplatin.[4,5]

According to a first aspect of the present invention there is provided a pharmaceutical composition for the treatment of cancer comprising an effective amount of a compound having two gold(I) atoms each covalently bonded to a carbon atom in a covalent link connecting the two gold(I) atoms and a pharmaceutically acceptable excipient.

A second aspect of the present invention provides a compound having two gold(I) atoms each covalently bonded to a carbon atom in a covalent link connecting the two gold(I) atoms for use as a chemotherapeutic agent.

A third aspect of the present invention provides the use of a compound having two gold(I) atoms each covalently bonded to a carbon atom in a covalent link connecting the two gold(I) atoms in the preparation of a medicament for the treatment of cancer.

A fourth aspect of the present invention provides a method of treating a cancer in a human or animal patient comprising administering to said patient a therapeutically effective amount of a compound having two gold(I) atoms each covalently bonded to a carbon atom in a covalent link connecting the two gold(I) atoms.

The present invention is based on the observation that compounds comprising two gold(I) atoms each covalently bonded to a carbon atom in a covalent link connecting the two gold(I) atoms exhibit unexpectedly high potency in cell toxicity studies and DNA cross-linking assays which indicate that pharmaceutical compositions comprising such compounds should show efficacy in the treatment of cancer. While not wishing to be limited to any particular theory, it is proposed that the high cell toxicity and cross-linking behaviour may be related to the provision of two gold(I) atoms in the inventive compounds which facilitates DNA cross-linking. It is further postulated that this effect may be enhanced by the relatively high stability of the gold(I)-carbon covalent bonds arising, at least partially, as a result of the similarity in electronegativity of gold(I) and carbon. This explanation should not, however, be taken as limiting the scope of the present invention in any way.

It has been observed that compounds forming part of the present invention are much more potent than the platinum drugs across cell lines which are sensitive to the platinum drugs and cell lines which are resistant to the platinum drugs. The present invention therefore provides chemotherapeutic agents which are likely to exhibit significantly improved efficacy in cancer treatment compared to the platinum drugs.

Furthermore, the inventive compounds show especially high potency in cell lines which are cisplatinum or carboplatinum resistant. The present invention therefore provides chemotherapeutic agents which should be particularly effective in treating cancers which are no longer responsive to treatment with the platinum drugs.

The present invention therefore represents an important step forward in the treatment of cancer, especially in cases where the tumour cells have developed a resistance to the platinum drugs.

Preferably the chemotherapeutic agent employed in the invention (i.e. the compound having two gold (I) atoms each covalently bonded to a carbon atom) has a first gold(I) atom covalently bonded to a first carbon atom and a second gold(I) atom covalently bonded to a second carbon atom. Said compound preferably comprises a substituted or unsubstituted aromatic group as part of the covalent link.

It is preferred that the first carbon atom is part of a substituted or unsubstituted aromatic group, i.e. said first carbon atom is preferably a ring carbon atom forming part of a substituted or unsubstituted aromatic group. The substituted or unsubstituted aromatic group may be a substituted or unsubstituted phenyl group.

The second carbon atom may be part of a substituted or unsubstituted alkyl, alkene, alkyne, aryl or aromatic group. Preferably the aromatic group of which the second carbon atom is a part is a substituted or unsubstituted phenyl group.

In a preferred embodiment the inventive compound incorporates a moiety represented by formula 1:

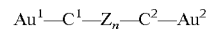

$$Au^1\text{—}C^1\text{—}Z_n\text{—}C^2\text{—}Au^2 \qquad \text{Formula 1}$$

where: $Au^1$ is the first gold (I) atom; $Au^2$ is the second gold (I) atom; $C^1$ is the first carbon atom; $C^2$ is the second carbon atom; Z is a linking group; and n is 0 or 1, i.e. a linking group may or may not be provided between the first and second carbon atoms.

In further preferred embodiments of the invention the chemotherapeutic agent incorporates a ligand bonded to each of said gold(I) atoms, each of said ligands being selected from the group consisting of $PR_3$, $P(OR)_3$, CNR, NCR, $PR_n(CH_2OR^\ddagger)_{3-n}$, $N_4C_6H_{12}$, $[N_4C_6H_{12}\text{—}N\text{—}CH_3]^+$, $PN_3C_6H_{12}$, and $P[N_3C_6H_{12}\text{—}N\text{—}CH_3]^+$, where R is a substituted or unsubstituted hydrocarbon moiety and $R^\ddagger$ is selected from the group consisting of H, Me, $SO_2^-$, $PO_3^-$, alkyl and aryl, and each $R^\ddagger$ in any one ligand is the same or different. Preferably R is a substituted or unsubstituted alkyl, alkene, alkyne, aryl or aromatic group and each R in any one ligand is the same or different. Moreover, R may be selected from the group consisting of methyl, ethyl, propyl, butyl and phenyl groups. In a particularly preferred embodiment of the invention, the ligand is $PPh_3$.

An "effective amount" of a pharmaceutical composition of the present invention is an amount that, when administered to a patient, ameliorates a symptom of a specific disease or condition to be treated. An effective amount of a composition of the present invention can be determined by one skilled in the art by administering a quantity of the composition to a patient and observing the result. In addition, those skilled in the art are familiar with identifying patients having the particular disease or condition and are readily able to identify patients who suffer from these diseases or conditions.

The inventive compositions may be administered by any route as conventionally employed for chemotherapeutic agents.

The compositions of the present invention can be administered to a patient alone or as part of a composition that contains other components such as excipients, diluents, and carriers, all of which are well-known in the art. The compositions can be administered to humans and animals either orally, rectally, parenterally (intravenous, by intramuscularly or subcutaneously), intracisternally, intravaginally, intraperitoneally (which may be particularly suitable for treating ovarian cancer), intrathecally, intravescially, locally (powders, ointments or drops), or as a buccal or nasal spray.

Compositions suitable for parenteral injection can comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying and dispensing agents. Prevention of the action of microorganisms can be ensured by various antibacterial and antifungal agents, for example, parbens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminium monostearate and gelatin.

Solid dosage forms for oral administration include capsules, tablets, pills, powders, and granules. In such solid dosage forms, the active agent is admixed with at least one customary inert excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example, paraffin; (f) absorption accelerators, as for example quaternary ammonium complexes; (g) wetting agents, as for example, acetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage form such as tablets, capsules, pills, and granules can be prepared with coatings and shells, such as enteric coatings and others well-known in the art. They may contain pacifying agents and can also be of such composition that they release the active agent or agents in a certain part of the intestinal tract in a delayed manner. Examples of embedding compositions which can be used are polymeric substances and waxes. The active agents can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active agents, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1.3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvents, such as wetting agents, emulsifying and suspending agents, sweetening, flavouring, and perfuming agents.

Suspensions, in addition to the active agents, can contain suspending agents, as for example, ethoxylated isostearyl alcohols, polyoxyethylene sorbitol and sorbitan esters, microcrystalline cellulose, aluminium metahydroxide, bentonite, agar-agar and tragacanth, or mixtures of these substances, and the like.

Compositions for rectal administrations are preferably suppositories which can be prepared by mixing the compositions of the present invention with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a composition of this invention include ointments, powders, sprays and inhalants. The active agent is admixed under sterile conditions with a physiologically acceptable carrier and any preservative, buffers, or propellants as may be required. Ophthalmic formulations, eye ointments, powders, and solutions are also contemplated as being within the scope of this invention.

The active compound of the present invention can be administered to a patient at dosage levels in the range of about 0.1 to about 1,000 mg per day. For a normal human adult having a body weight of about 70 kilograms, a dosage in the range of about 0.01 to about 7000 mg per kilogram of body weight per day is sufficient. The specific dosage used, however, can vary. For example, the dosage can depend on a number of factors including the requirements of the patient, the severity of the condition being treated, and the pharmacological activity of the composition being used. The determination of optimum dosages for a particular patent is well-known to those skilled in the art. In the case of intravenous administration, the chemotherapeutic agents may be given to the patient up to twelve times with a gap of up to approximately four weeks between each treatment. In this case the intravenous administration may be injection into a vein over a relatively short period of time, e.g. a few minutes, or through a drip by intravenous infusion over longer periods of time, such as between about 30 minutes and a few hours. Alternatively, the agents may be administered intravenously by continuous infusion (also known as protracted venous infusion or ambulant infusion) over longer periods of time, e.g. from a few days up to a number of weeks or months, by use of an infusion pump via a central line.

In addition, the compositions of the present invention can exist in unsolvated as well as solvated forms with pharmaceutically acceptable solvents such as water, ethanol, and the like. In general, the solvated forms are considered equivalent to the unsolvated forms for the purposes of the present invention.

The composition of the present invention can be coadministered with an additional therapeutic agent. This therapeutic can include, but is not limited to, chemotherapeutic agents. Preferably, the composition of the present invention and the coadministered therapeutic agent work in conjunction with one another to create a more sustained effect. These two therapeutic agents can be either administered in one pharmaceutically acceptable carrier or separately.

The chemotherapeutic agent may be administered to a patient as an adjuvant to surgery or radiotherapy.

A first class of preferred compounds forming part of the present invention is represented by formula 2:

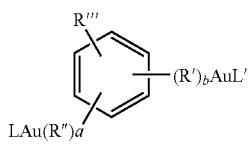

Formula 2

Where: L and L' are ligands; R' and R" are substituted or unsubstituted divalent hydrocarbon moieties; a is 0 to 3; and b is 0 to 3. The substitution pattern on the aromatic ring of the gold moieties may be ortho, meta or para.

R'" may be H, $SO_3^-$, $PO_4^{2-}$, $CO_2H$, OH, $(CH_2)_nCH_3$, $O(CH_2)_nCH_3$, $S(CH_2)_nCH_3$, an amino acid group, a substituted or subsubstituted linear or branched alkyl group or moiety containing from 1 to 6 carbon atoms (e.g. $C_1$-$C_4$ alkyl group or moiety, methyl, ethyl, n-propyl, i-propyl, butyl, i-butyl or t-butyl), which, if substituted, may carry one or two substituents (e.g. halogen, cyano, nitro, amino, alkoxy, hydroxyl, aryl, heteroaryl, an ester —$CO_2R^1$, wherein $R^1$ is hydrogen or methyl or ethyl, and an amide $C(O)NHR^2$ wherein $R^2$ is hydrogen or methyl or ethyl), an amino group NR""C(O)(R"''') where R"" and R"''' may be the same or different and R"" and R"''' are individually selected from the group consisting of H, alkyl (e.g. $(CH_2)_nCH_3$ wherein n is 0 to 6), aryl, heteroaryl, cycloalkyl and may together form a (optionally heteroatom containing) ring, a substituted or unsubstituted aryl (e.g. a $C_6$-$C_{10}$ aryl group such as phenyl or naphthyl, optionally carrying 1, 2, 3 or 4 substituents (e.g. cyano, halogen, nitro, trifluoromethyl, alkyl, alkylthio, alkoxy and hydroxyl)) or a substituted or unsubstituted heterocyclic group such as a heteroaryl group (e.g. having a 5- to 10-membered aromatic ring, such as a 5- or 6-membered ring, containing at least one heteroatom selected from O, S and N (e.g. pyridyl, pyrazinyl, pyrimidinyl, pyridazinyl, furanyl, thienyl, pyrazolidinyl, pyrrolyl and pyrazolyl groups)) or a non-aryl heterocyclic group (e.g. tetrahydrofuranyl or pyrrolidinyl) which may be substituted with a cyano, nitro, halogen, alkyl, alkylthio, alkoxy and hydroxyl group.

Preferred examples of this class of compound are selected from the group consisting of:

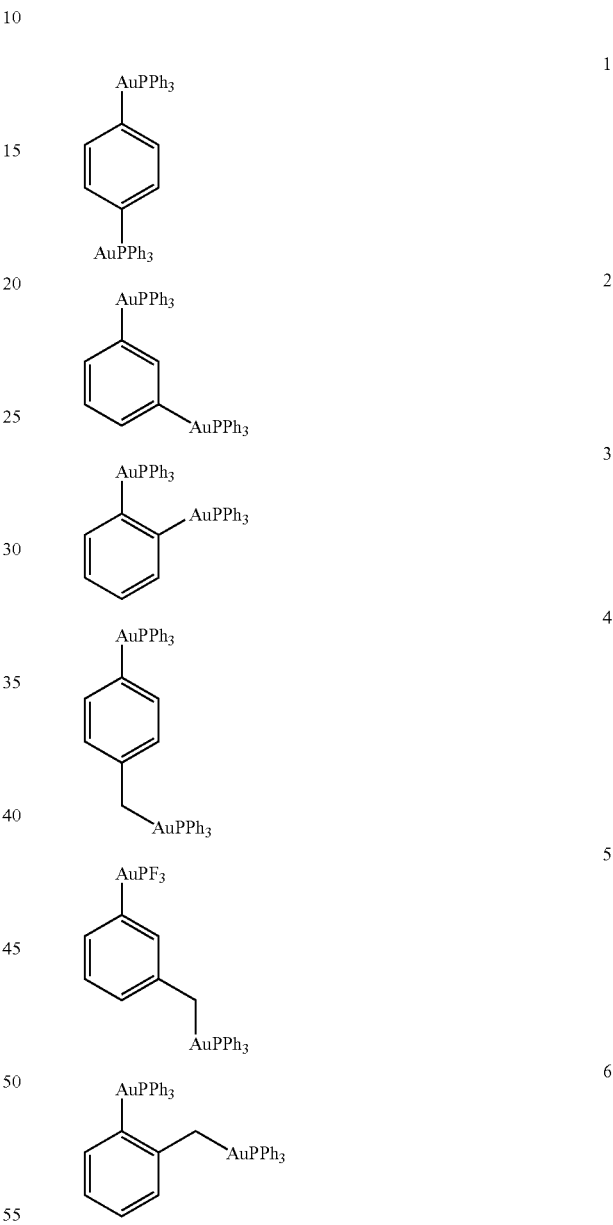

A second class of compounds forming part of the present invention is represented by formula 3:

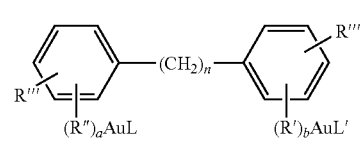

Formula 3

Where: L and L' are ligands; R' and R" are substituted or unsubstituted divalent hydrocarbon moieties; a is 0 to 3; and b is 0 to 3. The substitution pattern on the aromatic ring of the gold moieties may be ortho, meta or para.

R''' may be H, $SO_3^-$, $PO_4^{2-}$, $CO_2H$, OH, $(CH_2)_nCH_3$, $O(CH_2)_nCH_3$, $S(CH_2)_nCH_3$, an amino acid group, a substituted or subsubstituted linear or branched alkyl group or moiety containing from 1 to 6 carbon atoms (e.g. $C_1$-$C_4$ alkyl group or moiety, methyl, ethyl, n-propyl, i-propyl, butyl, i-butyl or t-butyl), which, if substituted, may carry one or two substituents (e.g. halogen, cyano, nitro, amino, alkoxy, hydroxyl, aryl, heteroaryl, an ester —$CO_2R^1$, wherein $R^1$ is hydrogen or methyl or ethyl, and an amide $C(O)NHR^2$ wherein $R^2$ is hydrogen or methyl or ethyl), an amino group NR""C(O)(R""') where R"" and R""' may be the same or different and R"" and R""' are individually selected from the group consisting of H, alkyl (e.g. $(CH_2)_nCH_3$ wherein n is 0 to 6), aryl, heteroaryl, cycloalkyl and may together form a (optionally heteroatom containing) ring, a substituted or unsubstituted aryl (e.g. a $C_6$-$C_{10}$ aryl group such as phenyl or naphthyl, optionally carrying 1, 2, 3 or 4 substituents (e.g. cyano, halogen, nitro, trifluoromethyl, alkyl, alkylthio, alkoxy and hydroxyl)) or a substituted or unsubstituted heterocyclic group such as a heteroaryl group (e.g. having a 5- to 10-membered aromatic ring, such as a 5- or 6-membered ring, containing at least one heteroatom selected from O, S and N (e.g. pyridyl, pyrazinyl, pyrimidinyl, pyridazinyl, furanyl, thienyl, pyrazolidinyl, pyrrolyl and pyrazolyl groups)) or a non-aryl heterocyclic group (e.g. tetrahydrofuranyl or pyrrolidinyl) which may be substituted with a cyano, nitro, halogen, alkyl, alkylthio, alkoxy and hydroxyl group.

Preferred examples of this class of compound are selected from the group consisting of:

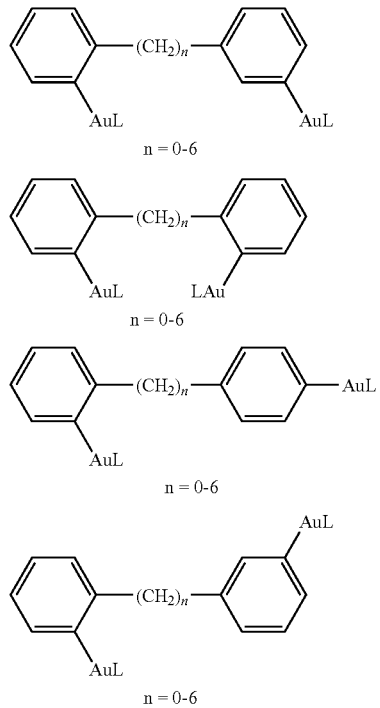

-continued

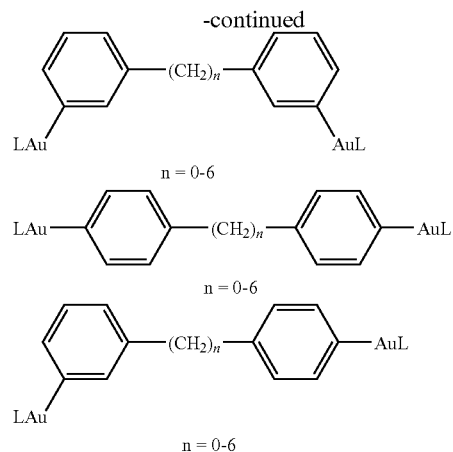

A third class of compounds forming part of the present invention is represented by formula 4:

Formula 4

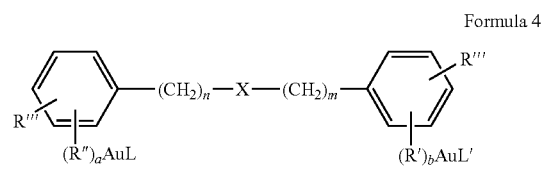

Where: L and L' are ligands; R' and R" are substituted or unsubstituted divalent hydrocarbon moieties; a is 0 to 3; and b is 0 to 3; and X is a linking group. X may be selected from the group consisting of: O, S, PR or NR in which R is a substituted or unsubstituted hydrocarbon moiety. The substitution pattern on each aromatic ring of the gold moieties may be ortho, meta or para.

R''' may be H, $SO_3^-$, $PO_4^{2-}$, $CO_2H$, OH, $(CH_2)_nCH_3$, $O(CH_2)_nCH_3$, $S(CH_2)_nCH_3$, an amino acid group, a substituted or subsubstituted linear or branched alkyl group or moiety containing from 1 to 6 carbon atoms (e.g. $C_1$-$C_4$ alkyl group or moiety, methyl, ethyl, n-propyl, i-propyl, butyl, i-butyl or t-butyl), which, if substituted, may carry one or two substituents (e.g. halogen, cyano, nitro, amino, alkoxy, hydroxyl, aryl, heteroaryl, an ester —$CO_2R^1$, wherein $R^1$ is hydrogen or methyl or ethyl, and an amide $C(O)NHR^2$ wherein $R^2$ is hydrogen or methyl or ethyl), an amino group NR""C(O)(R""') where R"" and R""' may be the same or different and R"" and R""' are individually selected from the group consisting of H, alkyl (e.g. $(CH_2)_nCH_3$ wherein n is 0 to 6), aryl, heteroaryl, cycloalkyl and may together form a (optionally heteroatom containing) ring, a substituted or unsubstituted aryl (e.g. a $C_6$-$C_{10}$ aryl group such as phenyl or naphthyl, optionally carrying 1, 2, 3 or 4 substituents (e.g. cyano, halogen, nitro, trifluoromethyl, alkyl, alkylthio, alkoxy and hydroxyl)) or a substituted or unsubstituted heterocyclic group such as a heteroaryl group (e.g. having a 5- to 10-membered aromatic ring, such as a 5- or 6-membered ring, containing at least one heteroatom selected from O, S and N (e.g. pyridyl, pyrazinyl, pyrimidinyl, pyridazinyl, furanyl, thienyl, pyrazolidinyl, pyrrolyl and pyrazolyl groups)) or a non-aryl heterocyclic group (e.g. tetrahydrofuranyl or pyrrolidinyl) which may be substituted with a cyano, nitro, halogen, alkyl, alkylthio, alkoxy and hydroxyl group.

Preferred examples of this class of compound are selected from the group consisting of:

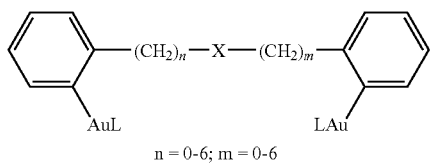
n = 0-6; m = 0-6

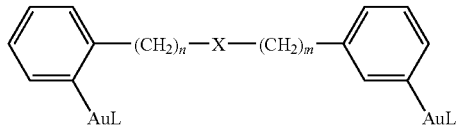
n = 0-6; m = 0-6

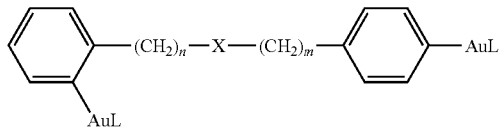
n = 0-6; m = 0-6

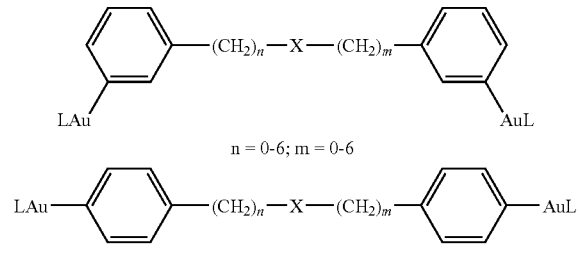
n = 0-6; m = 0-6

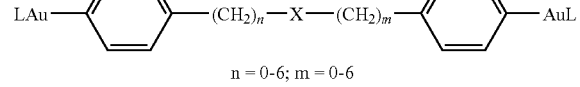
n = 0-6; m = 0-6

A fourth class of compounds forming part of the present invention is represented by formula 5:

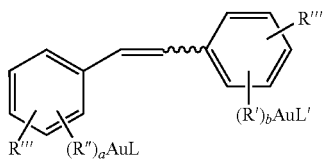

Formula 5

Where: L and L' are ligands; R' and R" are substituted or unsubstituted divalent hydrocarbon moieties; a is 0 to 3; and b is 0 to 3. The substitution pattern on the aromatic ring of the gold moieties may be ortho, meta or para.

R'" may be H, $SO_3^-$, $PO_4^{2-}$, $CO_2H$, OH, $(CH_2)_nCH_3$, $O(CH_2)_nCH_3$, $S(CH_2)_nCH_3$, an amino acid group, a substituted or subsubstituted linear or branched alkyl group or moiety containing from 1 to 6 carbon atoms (e.g. $C_1$-$C_4$ alkyl group or moiety, methyl, ethyl, n-propyl, i-propyl, butyl, i-butyl or t-butyl), which, if substituted, may carry one or two substituents (e.g. halogen, cyano, nitro, amino, alkoxy, hydroxyl, aryl, heteroaryl, an ester —$CO_2R^1$, wherein $R^1$ is hydrogen or methyl or ethyl, and an amide $C(O)NHR^2$ wherein $R^2$ is hydrogen or methyl or ethyl), an amino group N""C(O)(R""') where R"" and R""' may be the same or different and R"" and R""' are individually selected from the group consisting of H, alkyl (e.g. $(CH_2)_nCH_3$ wherein n is 0 to 6), aryl, heteroaryl, cycloalkyl and may together form a (optionally heteroatom containing) ring, a substituted or unsubstituted aryl (e.g. a $C_6$-$C_{10}$ aryl group such as phenyl or naphthyl, optionally carrying 1, 2, 3 or 4 substituents (e.g. cyano, halogen, nitro, trifluoromethyl, alkyl, alkylthio, alkoxy and hydroxyl)) or a substituted or unsubstituted heterocyclic group such as a heteroaryl group (e.g. having a 5- to 10-membered aromatic ring, such as a 5- or 6-membered ring, containing at least one heteroatom selected from O, S and N (e.g. pyridyl, pyrazinyl, pyrimidinyl, pyridazinyl, furanyl, thienyl, pyrazolidinyl, pyrrolyl and pyrazolyl groups)) or a non-aryl heterocyclic group (e.g. tetrahydrofuranyl or pyrrolidinyl) which may be substituted with a cyano, nitro, halogen, alkyl, alkylthio, alkoxy and hydroxyl group.

Preferred examples of this class of compound are selected from the group consisting of:

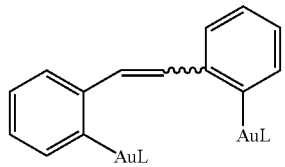

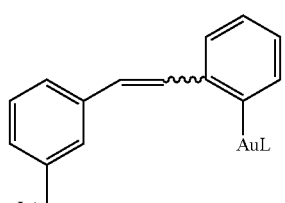

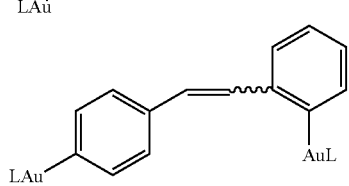

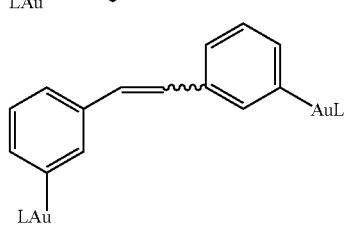

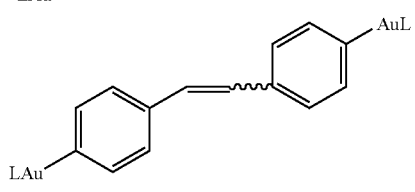

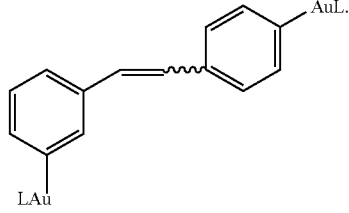

A fifth class of compounds forming part of the present invention is represented by formula 6:

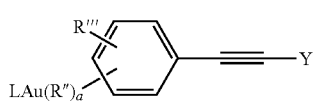

Formula 6

Where: Y is selected from the group consisting of: $(R')_b AuL'$ and

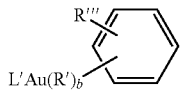

Where: L and L' are ligands; R' and R" are substituted or unsubstituted divalent hydrocarbon moieties; a is 0 to 3; and b is 0 to 3. The substitution pattern on the aromatic ring of the gold moieties may be ortho, meta or para.

R''' may be H, $SO_3^-$, $PO_4^{2-}$, $CO_2H$, OH, $(CH_2)_n CH_3$, $O(CH_2)_n CH_3$, $S(CH_2)_n CH_3$, an amino acid group, a substituted or subsubstituted linear or branched alkyl group or moiety containing from 1 to 6 carbon atoms (e.g. $C_1$-$C_4$ alkyl group or moiety, methyl, ethyl, n-propyl, i-propyl, butyl, i-butyl or t-butyl), which, if substituted, may carry one or two substituents (e.g. halogen, cyano, nitro, amino, alkoxy, hydroxyl, aryl, heteroaryl, an ester —$CO_2R^1$, wherein $R^1$ is hydrogen or methyl or ethyl, and an amide $C(O)NHR^2$ wherein $R^2$ is hydrogen or methyl or ethyl), an amino group NR''''C(O)(R''''') where R'''' and R''''' may be the same or different and R'''' and R''''' are individually selected from the group consisting of H, alkyl (e.g. $(CH_2)_n CH_3$ wherein n is 0 to 6), aryl, heteroaryl, cycloalkyl and may together form a (optionally heteroatom containing) ring, a substituted or unsubstituted aryl (e.g. a $C_6$-$C_{10}$ aryl group such as phenyl or naphthyl, optionally carrying 1, 2, 3 or 4 substituents (e.g. cyano, halogen, nitro, trifluoromethyl, alkyl, alkylthio, alkoxy and hydroxyl)) or a substituted or unsubstituted heterocyclic group such as a heteroaryl group (e.g. having a 5- to 10-membered aromatic ring, such as a 5- or 6-membered ring, containing at least one heteroatom selected from O, S and N (e.g. pyridyl, pyrazinyl, pyrimidinyl, pyridazinyl, furanyl, thienyl, pyrazolidinyl, pyrrolyl and pyrazolyl groups)) or a non-aryl heterocyclic group (e.g. tetrahydrofuranyl or pyrrolidinyl) which may be substituted with a cyano, nitro, halogen, alkyl, alkylthio, alkoxy and hydroxyl group.

In preferred embodiments of the invention L and L' are the same. Furthermore, preferably R' and R" are the same.

Preferred examples of this class of compound are selected from the group consisting of:

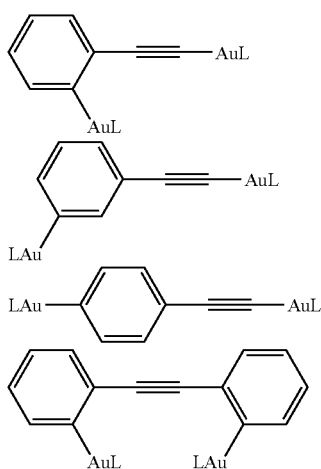

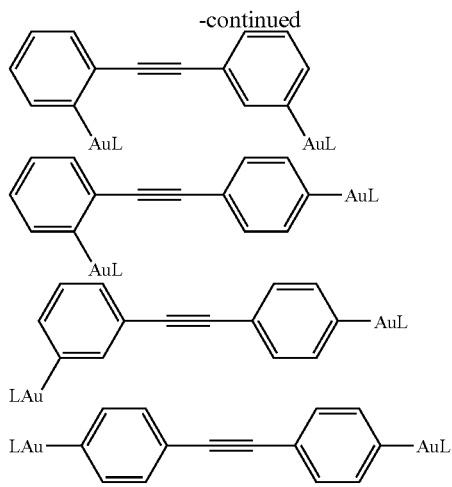

In formulae 2-6, L and L' may be the same or different. L and/or L' may be selected from the group consisting of $PR_3$, $P(OR)_3$, CNR, NCR, $PR_n(CH_2OR^{\ddagger})_{3-n}$, $N_4C_6H_{12}$ (hexamethylenetetraamine), $[N_4C_6H_{12}-N-CH_3]^+$, $PN_3C_6H_{12}$, and $P[N_3C_6H_{12}-N-CH_3]^+$, where R is any desirable substituted or unsubstituted hydrocarbon moiety e.g. a substituted or unsubstituted alkyl, alkene, alkyne, aryl or aromatic group. Thus R may be selected from the group consisting of methyl, ethyl, propyl, butyl and phenyl groups. It is particularly preferred that each R group in $PR_3$ is phenyl and that the ligand is $PPh_3$. Moreover, R' and R" may each be independently selected from the group consisting of methylene, ethylene, propylene, butylene and phenylene groups. $R^{\ddagger}$ is selected from the group consisting of H, $SO_2^-$, $PO_3^-$, alkyl (in particular methyl) and aryl, and each $R^{\ddagger}$ in any one ligand may be the same or different. Additionally, L and/or L' may be selected to control the solubility of the compound. Suitable ligands include glycols, polyethers, crown ethers and sugars. For compounds containing a plurality of phosphine ligands then two or more of the phosphine ligands may be linked through a PEG linker, crown ether or the like.

It is envisaged that compounds can be prepared that function as prodrugs to the active gold(I) containing compounds, which would be administered in one form and then converted, in vivo, to the active gold(I) containing form. Accordingly, the further aspects of the present invention relate to prodrugs to the active gold(I) containing compounds in which at least one of the gold(I) atoms is substituted by a gold(III) atom which is reducible, in vivo, to a gold(I) atom.

A fifth aspect of the present invention provides a pharmaceutical composition for the treatment of cancer comprising an effective amount of a compound having a first gold atom which is a gold(III) atom and a second gold atom which is either a gold(I) atom or a gold(III) atom, each of said first and second gold atoms being covalently bonded to a carbon atom in a covalent link connecting the first and second gold atoms, and the or each gold(III) atom being reducible, in vivo, to a gold(I) atom, and a pharmaceutically acceptable excipient.

A sixth aspect of the present invention provides a compound having a first gold atom which is a gold(III) atom and a second gold atom which is either a gold(I) atom or a gold (III) atom, each of said first and second gold atoms being covalently bonded to a carbon atom in a covalent link connecting the first and second gold atoms, and the or each gold(III) atom being reducible, in vivo, to a gold(I) atom for use as a chemotherapeutic agent.

A seventh aspect of the present invention provides for use of a compound having a first gold atom which is a gold(III) atom and a second gold atom which is either a gold(I) atom or a gold(III) atom, each of said first and second gold atoms being covalently bonded to a carbon atom in a covalent link connecting the first and second gold atoms, and the or each gold(III) atom being reducible, in vivo, to a gold(I) atom in the preparation of a medicament for the treatment of cancer.

An eighth aspect of the present invention provides method of treating a cancer in a human or animal patient comprising administering to said patient a therapeutically effective amount of a compound having a first gold atom which is a gold(III) atom and a second gold atom which is either a gold(I) atom or a gold(III) atom, each of said first and second gold atoms being covalently bonded to a carbon atom in a covalent link connecting the first and second gold atoms, and the or each gold(III) atom being reducible, in vivo, to a gold(I) atom.

Preferably said second gold atom is a gold(III) atom.

It will be appreciated that an appropriate number of ligands should be provided on each gold(III) atom present in compounds forming part of the fifth, sixth, seventh and eighth aspects of the present invention. Accordingly, where a gold(I) atom is substituted for a gold(III) atom to provide a prodrug to the active gold(I) containing compound, the single L or L' group which would have been bonded to the gold(I) atom should be substituted with three L or L' groups. The overall charge on the compound can be preselected by appropriate selection of ligands, for example, to provide a neutral gold (III) containing compound three anionic ligands, each carrying a charge of −1, can be chosen. Suitable ligands, e.g. porphyrin or crown ethers, can be employed in the gold(III) containing compounds to manipulate the solubility of the compound.

The invention is illustrated with reference to the following non-limiting Example and accompanying drawings, in which:

FIG. 1 is a graphical representation of DNA cross-linking in parental and resistant cell lines following treatment with cisplatinum;

FIG. 2 is a graphical representation of DNA cross-linking in parental and resistant cell lines following treatment with carboplatinum;

FIG. 3 is a graphical representation of DNA cross-linking in parental and platinum-resistant cell lines following treatment with compound A;

FIG. 4 is a graphical representation of DNA cross-linking in parental and platinum-resistant cell lines following treatment with compound B;

FIG. 5 is a graphical representation of DNA cross-linking in parental and platinum-resistant cell lines following treatment with compound C;

FIG. 6 is a graphical representation of DNA cross-linking in parental and platinum-resistant cell lines following treatment with compound D;

FIG. 7 is a graphical representation of DNA cross-linking in parental and platinum-resistant cell lines following treatment with compound E;

FIG. 8 is a graphical representation of DNA cross-linking in parental and platinum-resistant cell lines following treatment with compound F; and FIG. 9 is a graphical representation of DNA cross-linking in parental and platinum-resistant cell lines following treatment with a mono-gold compound, phenylgoldtriphenylphospine (PAuP), for comparison with the di-gold compounds of the present invention.

EXAMPLE

A comparison of the chemotherapeutic activity of compounds A-F (below) and that of cisplatinum and carbonplatinum was made using a series of paired cell lines that are known to be either sensitive or have acquired resistance to the clinically useful agents cisplatinum and carboplatinum. For details of the synthesis of compound A see Appendix A.

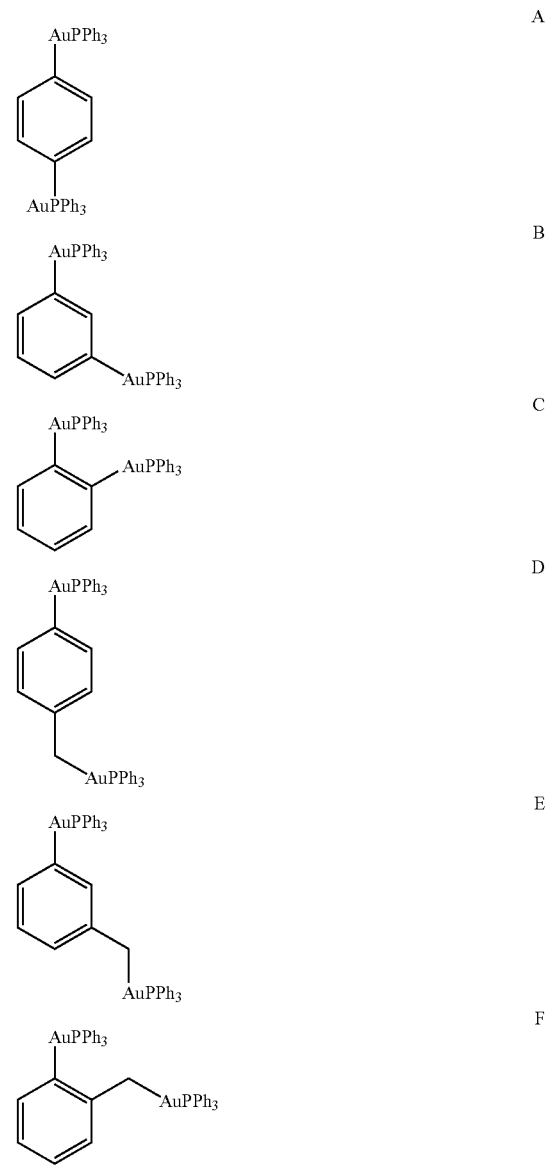

The sensitivities of the cell lines to cisplatinum, carboplatinum, and compounds A-F were determined using a growth inhibition assay which was a modified version of the MTT method (modified version of MTT method described in Appendix B).

The following is a brief description of the eleven different cell lines used in the growth inhibition assay:

The A2780 cell line (1 in FIGS. 1-9) is a human ovarian cell line which is sensitive to cisplatinum and carboplatinum. The A2780cis (2) and A2780carb (3) cell lines are modified versions of the A2780 cell line which exhibit cisplatinum and carboplatinum resistance respectively. Cell lines mcp1 (4) and mcp8 (5) are platinum-resistant A2780 sublines which are miss-match repair deficient.

The cor123 (6) is a non small cell lung cancer cell line which is sensitive to the platinum drugs. The cor123/cpr (7) cell line is a modified version of the cor123 cell line which has been modified to be resistant to cisplatinum and carboplatinum.

The ccu24 (8) cell line is an epithelial ovarian cancer cell line, developed at the Christie Hospital from a tumour biopsy, and the ccu24/cpr (9) cell line is a modified version of this cell line which is cisplatinum and carboplatinum resistant.

L1210 (10) is a murine leukemia cell line and L1210/M1140 (11) is its platinum drug resistant subline.

Table 1 illustrates the results of a first series of assays which were carried out to investigate the activity of each of the six inventive compounds (A-F) and cisplatinum. Table 2 illustrates the results of a further series of assays carried out on compounds A-F, and carboplatinum.

a) The A2780cis cell line ($IC_{50}$ 0.2 nM) is over sixty-times more sensitive to compound A than the parental (sensitive) A2780-S line ($IC_{50}$ 13.4 nM); and b) The A2780carb cell line ($IC_{50}$ 0.6 nM) is over twenty-times more sensitive to compound A than the parental A2780-S line ($IC_{50}$ 13.4 nM).

3) Compounds containing more than one Au(I) atom are more potent than the mono-gold compound.

This collateral sensitivity is seen in both mouse and human tumour cell lines.

Preliminary studies have been carried out to investigate the mechanism underlying this increased sensitivity. These studies were carried out using the Comet assay (described in Appendix C), which measures damage to DNA. The results are shown in FIGS. 1 (cisplatinum), 2 (carboplatinum), 3 to 8 (compounds A-F) and 9 (phenylgoldtriphenylphospine, PAuP).

It can be seen from FIGS. 1 and 2 that both cisplatinum and carboplatinum cause extensive DNA cross-linking in the parental (platinum-sensitive) A2780, L1210, and cor123 cell lines, whereas much less cross-linking is seen in the plati-

TABLE 1

$IC_{50}$ (nM) of compounds tested.

| | Cell line | | | | | | | | | |
|---|---|---|---|---|---|---|---|---|---|---|
| Drug | A2780-S | A2780 cis | A2780 carb | cor123 | cor123/cpr | ccu24 | ccu24/cpr | L1210 | L1210/M1140 | mcp1 | mcp8 |
| A | 13.4 | 0.2 | 0.6 | 19.3 | 1.5 | 25.3 | 3.6 | 38.3 | 6.4 | 0.5 | 0.6 |
| B | 9.8 | 0.2 | 0.4 | 12.6 | 1.2 | 18.7 | 2.1 | 26.6 | 4.1 | 0.4 | 0.4 |
| C | 12.8 | 0.3 | 0.5 | 14.4 | 1.4 | 20.2 | 3.3 | 42.7 | 5.2 | 0.5 | 0.5 |
| D | 32.4 | 7.3 | 10.3 | 22.3 | 15.7 | 36.4 | 12.5 | 48.7 | 17.4 | 8.4 | 6.8 |
| E | 8.9 | 0.4 | 0.6 | 17.7 | 1.4 | 10.2 | 2.4 | 32.5 | 5.3 | 0.9 | 0.9 |
| F | 20.4 | 5.4 | 7.3 | 28.2 | 11.4 | 22.1 | 9.5 | 28.1 | 11.4 | 6.3 | 5.3 |
| Cisplatin* | 1320 | 30460 | 27640 | 3430 | 26650 | 4320 | 24850 | 12140 | 44860 | 19860 | 24450 |
| PAuP* | >10000 | >10000 | | | | | | | | | |

*Comparative data.

TABLE 2

$IC_{50}$ values (nM) of compounds tested.

| | Cell line | | | | | | | | | |
|---|---|---|---|---|---|---|---|---|---|---|
| Drug | A2780-S | A2780 cis | A2780 carb | cor123 | cor123/cpr | ccu24 | ccu24/cpr | L1210 | L1210/M1140 | A2780/mcp1 | A2780/mcp8 |
| A | 16.5 | 0.5 | 0.9 | 22.2 | 4.5 | 28.3 | 6.4 | 41.6 | 9.2 | 3.5 | 4.6 |
| B | 12.1 | 0.6 | 0.7 | 15.8 | 4.3 | 21.8 | 5.1 | 29.6 | 7.2 | 3.5 | 5.4 |
| C | 15.2 | 0.6 | 0.8 | 17.6 | 4.4 | 23.2 | 6.3 | 45.8 | 8.4 | 3.5 | 4.6 |
| D | 36.6 | 10.2 | 13.5 | 25.4 | 19.7 | 39.5 | 15.6 | 50.3 | 20.6 | 19.5 | 14.8 |
| E | 11.2 | 0.7 | 0.9 | 21.1 | 4.4 | 13.5 | 5.4 | 35.6 | 8.5 | 3.9 | 4.7 |
| F | 24.3 | 8.3 | 10.4 | 31.1 | 14.6 | 26.4 | 12.2 | 31.2 | 14.4 | 10.4 | 11.4 |
| Carboplatin* | 1590 | 34580 | 32150 | 5350 | 29820 | 5820 | 27190 | 15320 | 47780 | 24780 | 26750 |

*Comparative data.

The results shown in Table 2 illustrate the reproducibility of the data shown in Table 1.

The data on the effects of compounds A-F on the eleven cell lines can be summarized as follows:

1) Compounds A-F are considerably more potent than the platinum drugs (nM compared to μM);

2) The inventive compounds A-F are more active in the platinum-resistant cell lines than in the parental cell lines. Taking compound A as an example:

num-resistant cell lines. This is in agreement with the hypothesis that DNA is the target for the platinum drugs and that resistance arises due to a reduction of DNA damage in the resistant cells. This can arise by a number of mechanisms including DNA repair, increased deactivation of drug, or decreased drug uptake.

In contrast, it can be seen from FIGS. 3 to 8 that compounds A-F cause more DNA damage in the platinum-resistant cell lines than in the parental (platinum-sensitive) cell lines.

FIG. 9 illustrates comparative data and shows the importance of having more than one gold atom in the molecule. The level of cross-linking seen with PAuP is low compared to the di-gold compounds. The mono-gold compound is also much less cytotoxic ($ID_{50}$>10000 mu, Table 1).

Table 3 illustrates the results of the following calculation using the DNA cross-linking results obtained in the Comet assays:

TABLE 3

Summary of DNA crosslinking (Comet) experiments. Au(III) is [Au(η2-$C_6H_4CH=NC_6H_5)Cl_2$], and Au(I) is [Au($C_6H_5$)(PPh$_3$)].

DNA cross-linking in the parental (sensitive) cell line
DNA cross-linking in the platinum drug resistant cell line

| Drug | A2780cis | A2780carb | cor123 | ccu24 | L1210 | A2780mcp1 | A2780/mcp8 |
|---|---|---|---|---|---|---|---|
| A | 0.50 | 0.53 | 0.56 | 0.40 | 0.69 | 0.59 | 0.60 |
| B | 0.36 | 0.37 | 0.38 | 0.39 | 0.47 | 0.40 | 0.39 |
| C | 0.36 | 0.36 | 0.38 | 0.37 | 0.71 | 0.38 | 0.41 |
| D | 0.54 | 0.63 | 0.62 | 0.47 | 0.63 | 0.48 | 0.50 |
| E | 0.39 | 0.40 | 0.43 | 0.46 | 0.40 | 0.41 | 0.48 |
| F | 0.52 | 0.61 | 0.62 | 0.60 | 0.53 | 0.54 | 0.56 |
| Cisplatin* | 5.65 | 8.08 | 5.72 | 4.65 | 3.37 | 5.40 | 5.70 |
| Au (III)* | 0.67 | 0.71 | 0.83 | 0.78 | 0.54 | 0.72 | 0.69 |
| Au (I)* | 1.00 | 1.33 | 0.75 | 1.00 | 1.33 | 1.33 | 1.33 |

*Comparative data.

The results for cisplatin show the expected trend of increased activity (i.e. a ratio greater than unity) in the parental cell lines compared to the platinum-resistant cell lines. Each of the inventive compounds (A-F) possess ratios of significantly below 1.00 for all of the resistant cell lines, thus confirming the above observation that compounds A-F cause more DNA cross-linking in the platinum-resistant cell lines than in the parental (platinum-sensitive) cell lines.

Compounds A-F therefore show enhanced cell killing in platinum-resistant cell lines in vitro, which is likely to be due to increased DNA damage in the platinum-resistant cell lines. The exact mechanism that underlies this has not yet been fully elucidated. However activity is seen in the platinum resistant miss-match repair deficient mcp1[6] and mcp8 cell lines. It is therefore proposed that the inventive compounds are likely to show enhanced activity in tumours that are mis-match repair deficient.

Compounds A-F are simple metal compounds and do not contain platinum. The ability of the inventive compounds to selectively kill platinum-resistant cells may have important clinical implications as resistance to platinum drugs is cited as a cause of the failure of therapy in a number of cancers including ovarian and lung.

APPENDIX A

Synthesis of the Compounds

All solvents were dried and distilled under an $N_2$ atmosphere prior to use. All chemicals were purchased from commercial sources apart from [ClAu($SC_4H_8$)] which was prepared by the literature method.[14]

Preparation of 1,4-bis-(triphenylphospinogold(I))benzene (A)

To 1,4-dibromobenzene (0.074 g, 0.31 mmol) dissolved in ether (20 mL) at −78° was added tertiary butyl lithium (0.75 mL, 1.25 mmol) and the reaction mixture allowed to stir for 30 min. To this mixture was added thiophene (5 mL) and [ClAu($SC_4H_8$)] (0.200 g, 0.62 mmol) and the reaction stirred for 1.5 hours. Triphenylphosphine (0.083 g, 0.32 mmol) was then added and the solution stirred for another 1.5 hours before warming to room temperature and stirring for another 30 min. The diethyl ether was then removed under reduced pressure, the crude material extracted into dichloromethane and filtered to remove lithium salts. The compound was then recrystallised from hot ether; yield 0.286 g, 93%. mp 139° decomp. NMR: $^1$H: 7.70-7.49 ppm aryl-H; $^{31}$P{$^1$H}: 44.8 ppm; $^{13}$C{$^1$H}: 168.0, 139.7, 133.3, 130.2, 128.1, 131.0 ppm; Microanalysis: Found C=50.2; H=3.9; P=6.0; Calc: C=50.7; H=3.4; P=6.2.

In a similar manner the compounds [1,4-bis-(LAu)$C_6H_4$] can be prepared where L is any desirable ligand, for example, CNBu$^t$, PEt$_3$, P(OMe)$_3$ or NCMe.

This experimental procedure can be extended to other polyaromatic systems. An example of which is 4,4'-bis-(triphenylphospinogold(I))biphenyl.

Preparation of 4,4'-bis-(triphenylphospinogold(I))biphenyl.

Method 1-Using [ClAu($SC_4H_8$)]

To 4,4'-dibromobiphenyl (0.096 g, 0.31 mmol) dissolved in ether (20 mL) at −78° was added tertiary butyl lithium (0.75 mL, 1.25 mmol) and the reaction mixture allowed to stir for 30 min. To this mixture was added thiophene (5 mL) and [ClAu($SC_4H_8$)] (0.200 g, 0.62 mmol) and the reaction stirred for 1.5 hours. Triphenylphosphine (0.083 g, 0.62 mmol) was then added and the solution stirred for another 1.5 hours before warming to room temperature and stirring for another 30 min. The diethyl ether was then removed under reduced pressure, the crude material extracted into dichloromethane and filtered to remove lithium salts. The compound was then recrystallised from hot ether; yield 0.275 g, 83%. mp 138° decomp. NMR: $^1$H: 7.70-7.47 ppm aryl-H; $^{31}$P{$^1$H}: 44.9 ppm; $^{13}$C{$^1$H}: 170.5, 139.9, 134.8, 131.6, 131.5, 129.5, 126.4 ppm; Microanalysis: Found: C=53.8, H=3.6, P=5.8; Calc: C=53.2; H=3.6; P=6.1.

In a similar manner the compounds [1,4-bis-(LAu)$C_6H_4$] can be prepared where L is any desirable ligand, for example, CNBu$^t$, PEt$_3$, P(OMe)$_3$ or NCMe.

Method 2-Using [ClAu(AsPh$_3$)]

To 4,4'-dibromobiphenyl (0.096 g, 0.31 mmol) dissolved in ether (20 mL) at −78° was added tertiary butyl lithium (0.75 mL, 1.25 mmol) and the reaction mixture allowed to stir for 30 min. To this mixture was added thiophene (5 mL) and [ClAu(AsPh$_3$)] (0.128 g, 0.62 mmol)[15] and the reaction stirred for 1.5 hours. Triphenylphosphine (0.083 g, 0.62 mmol) was then added and the solution stirred for another 1.5 hours before warming to room temperature and stirring for another 30 min. The diethyl ether was then removed under reduced pressure, the crude material extracted into dichloromethane and filtered to remove lithium salts. The compound was then recrystallised from hot ether; yield 0.265 g, 80%. mp 138° decomp. NMR: $^1$H: 7.70-7.47 ppm aryl-H; $^{31}$P{$^1$H}: 44.9 ppm; $^{13}$C{$^1$H}: 170.5, 139.9, 134.8, 131.6, 131.5, 129.5, 126.4 ppm; Microanalysis: Found: C=53.6, H=3.5, P=6.1; Calc: C=53.2; H=3.6; P=6.1.

In a similar manner the compounds [1,4-bis-(LAu)C$_6$H$_4$] can be prepared where L is any desirable ligand, for example, CNBu$^t$, PEt$_3$, P(OMe)$_3$ or NCMe.

4,4'-bis-(triphenylphospinogold(I))biphenyl has also been characterised by a single crystal X-ray diffraction study:

Crystal form: Monoclinic; Space Group P21/c; a=18.6224(2) Å; b=10.27190(10) Å; c=24.0682(3) Å; β=102.634°; Z=4; T=150 K; R$_1$=4.05.

Preparation of a Prodrug Compound Containing Two Gold (III) Atoms

Shown below is an example of a reaction scheme suitable for the preparation of a prodrug compound containing two gold(III) atoms, which would be reducible, in vivo, to gold(I) atoms.

R may be any required chemical group, e.g. hydrogen, methyl, ethyl, propyl etc.

APPENDIX B

Growth Inhibition Assay

The cell toxicity studies were performed using a modification of the method MTT.[7] The principle of the assay is to assess the growth inhibitory effect of a drug at various doses over a five-day time course. This assay was performed in 96-well microtitre plates. Cells were seeded at densities of 400-1,000 cells per well, depending on the doubling time of the cell line. All cell dilutions were performed in growth medium containing 10% FCS (foetal calf serum).

Compounds under investigation were dissolved in DMSO (dimethylsulphoxide). Serial dilutions of compound were made into the cell suspension, ensuring that the proportion of DMSO remained below 0.5%. 200 μl of cells and drug mix was added to the 96-well plates in triplicate. The plates were incubated for five days at 5% CO$_2$ and 37° C. After this time, the plates were removed from the incubator and 50 μl of a 3 mg/ml solution of MTT [3-(4,5-dimethyl-thiazol-2-yl)-2,5-diphenyl tetrazolium bromide] was added to each well and incubated in the same conditions for another 3 hours. The medium from each well was aspirated and the formazan crystals were solubilised in 200 μl of DMSO. The plates were read using a Multiskan platereader at 540 nm and 690 nm. Growth inhibition curves were constructed using mean and standard deviation of the triplicate absorbance values and from these curves the IC$_{50}$ values were calculated.

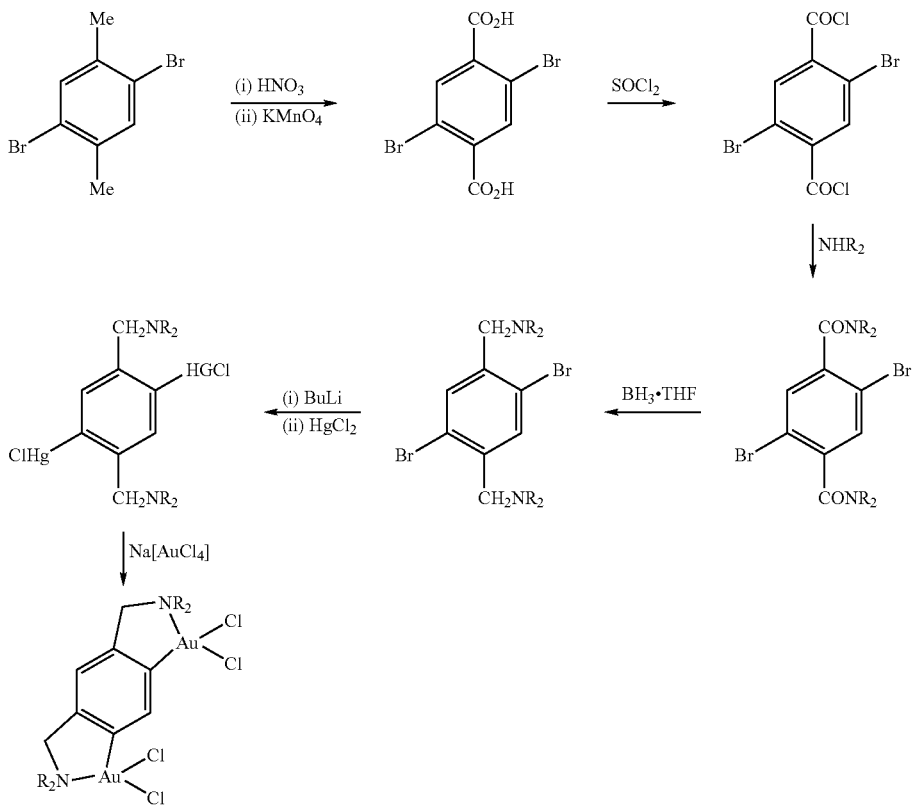

APPENDIX C

Comet Assay

DNA damage was measured by the single cell gel electrophoresis (SCGE) assay or "Comet assay", originally developed by Ostling and Johnson[8]. This is a method for determining the extent of DNA damage and repair capacity within individual cells.[9-11] It has previously been shown that this technique can be used to investigate the mechanism of action of different DNA damaging agents.[12]

Cells were trypsinised, suspended in 0.5 ml of ice cold fresh medium and transferred into plastic 24-well dishes prior to embedding in agarose. For the cross-linking studies treated and control samples were chilled on ice (to prevent any repair of DNA damage) and irradiated to a dose of 20 Gy in a Caesium-137 source (0.4 Gy/min). Control, (unirradiated, non-drug treated cells) were maintained on ice in the same manner as treated samples.

Glass microscope slides, frosted at one end, were pre-coated with 1% normal agarose in distilled water. These slides were allowed to air dry overnight prior to use. A 1% low melting point agarose (LMP) mixture in PBS was melted and held at 45° C. 1 ml of LMP was then added to 0.5 ml of cell suspension on ice and the resultant mixture was pipetted onto a pre-coated glass microscope slide and allowed to set for 1-2 minutes before being transferred to an ice tray. The slides were immersed in ice cold lysis solution (100 mM EDTA, 10 mM Tris-HCl, 1% Triton ×100, 1% DMSO, 2.5M NaCl) for 1 hr, and washed three times by immersion in fresh double distilled water for 15 minutes.

Slides were then placed onto a flat bed electrophoresis tank and covered (5-6 mm) with alkali unwinding solution (50 mM NaOH, 1 mM EDTA buffered to pH 12.5) and left under subdued lighting for 45 minutes to allow the DNA to unwind before being subjected to electrophoresis at 0.6V/cm for 25 minutes. Each slide was rinsed with 2×1 ml of 0.4M Tris-HCl, pH 8.0 and allowed to dry in air. The dried slides were then rehydrated for 20 minutes with double distilled water, 2×1 ml of propidium iodide solution (2.5 μg/ml) was added and staining was allowed to proceed for 15 minutes. Slides were then immersed in 1 litre of double distilled water for 1 hour to reduce excess background staining. The slides were cover slipped and then examined at 250× magnification under an epifluorescent microscope (Zeiss-Jenamed) using green light from a 50 watt mercury source with a 580 nm reflector and a 590 nm barrier filter set. Images were captured using an attached Sony HAD-1 interline CCD camera and Komet software analysis package (Kinetic Imaging). Twenty-five images from each of two duplicate slides were captured and analysed and the individual "comet moments" as defined by Olive et al[13], were calculated. The total fluorescence of the image represents the amount of DNA present and the length of the image, measured in pixels, represents the length of migration of the DNA. The head and tail areas of the image were identified and the intensity of each was determined. The tail moment is calculated by multiplying the fraction of DNA present in the tail by half the length of the tail.

REFERENCES

1. Hrubisko, M., McGown, A. T., Fox, B. W. "The role of metalothionein, glutathione, glutathione S-transferases and DNA repair in resistance to platinum drugs in a series of L1210 cell lines made resistant to platinum agents." *Biochemical Pharmacology*, 1993, 45, 253-256.
2. Fink, D., Aebi, S., Howell, S. B. "The role of DNA mismatch repair in drug resistance." *Clinical Cancer Research*, 1998, 4, 1-6.
3. *Chemical Reviews*, 1999, 9, 2589-2600.
4. *Critical Reviews in Oncology/Hematology*, 2002, 42, 225-248.
5. *Expert Reviews in Anticancer Therapy*, 2002, 2, 347-346.
6. Colella G; Marchini S; D'Incalci M. "Mismatch repair is associated with resistance to DNA minor groove alkylating agents." *British Journal of Cancer*, 1999, 80 (3-4), 338-343.
7. Alley, M. C., Scudiero, D. A., Monks, A., Hursey, M. L., Czerwinski, M. J., Fine, D. L., Abbott, B. J., Mayo, J. G., Shoemaker, R. H., Boyd, M. R. "Feasibility of drug screening with panels of human tumor cell lines using a microculture tetrazolium assay." *Cancer research*, 1988, 48, 589-601.
8. Ostling, O. and Johnson, J. "Microelectrophoretic studies of radiation induced DNA damage in individual mammalian cells." *Biochemical and Biophysical Research Communications*, 1984, 123, 29-298.
9. McKelvey-Martin, V. J., Green, M. H., Schmezer, P., Pool-Zobel, B. L., De Meo, M. P. and Collins, A. "The single cell gel electrophoresis assay (comet assay): a European review." *Mutatation Research*, 1993, 288, 47-63.
10. Collins, A. R., Fleming, I. M. and Gedik, C. M. "In vitro repair of oxidative and ultraviolet-induced DNA damage in supercoiled nucleoid DNA by human cell extract." *Biochimica et Biophysica Acta*, 1994, 1219, 724-727.
11. Olive, P. L. and Banath, J. P. "Sizing highly fragmented DNA in individual apoptotic cells using the comet assay and a DNA crosslinking agent." *Experimental Cell Research*, 1995, 221, 19-26.
12. Ward, T. H., Butler, J., Shahbakhti, H. and Richards, J. T. (1997). "Comet assay studies on the activation of two diaziridinylbenzoquinones in K562 cells." *Biochemical Pharmacology*, 1997, 53, 1115-1121.
13. Olive, P. L, Banath, J. P. and Durand, R. E. "Heterogeneity in radiation-induced DNA damage and repair in tumor and normal cells measured using the "comet" assay." *Radiation Research*, 1990, 122, 86-94.
14. R. Uson, A. Laguna, M. Laguna, *Inorganic Synthesis*, 1989, 26, 85-91.
15. *J. Organomet. Chem.*, 2002, 648, 1-7.

The invention claimed is:
1. A pharmaceutical composition for the treatment of cancer comprising an effective amount of a compound selected from the group consisting of:

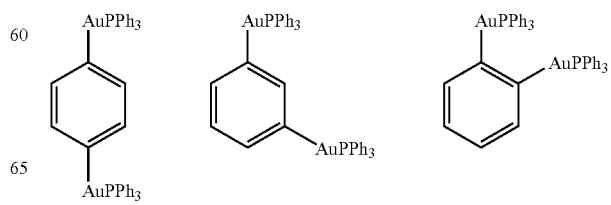

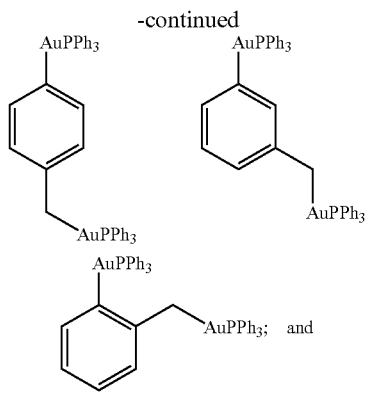

and a pharmaceutically acceptable excipient.

2. A pharmaceutical composition for the treatment of cancer comprising an effective amount of a compound having the formula:

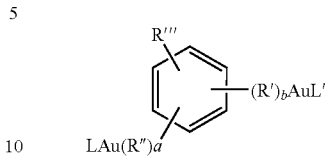

where: L and L' are $PPh_3$; R' and R'' are each independently selected from the group consisting of methylene, ethylene, propylene, butylene and phenylene groups; a is 0 to 3; b is 0 to 3; R''' is H; and a pharmaceutically acceptable excipient.

* * * * *